United States Patent
Kobayashi et al.

(10) Patent No.: US 7,164,043 B2
(45) Date of Patent: Jan. 16, 2007

(54) PROCESS FOR PRODUCING β-AMINOKETONE AND CATALYST THEREFOR

(75) Inventors: Shu Kobayashi, Tokyo (JP); Masaharu Sugiura, Kanagawa (JP)

(73) Assignee: Japan Science and Technology Agency, Saitama (JP)

( * ) Notice: Subject to any disclaimer, the term of this patent is extended or adjusted under 35 U.S.C. 154(b) by 198 days.

(21) Appl. No.: 10/507,027

(22) PCT Filed: Mar. 7, 2003

(86) PCT No.: PCT/JP03/02715

§ 371 (c)(1),
(2), (4) Date: Sep. 8, 2004

(87) PCT Pub. No.: WO03/076396

PCT Pub. Date: Sep. 18, 2003

(65) Prior Publication Data

US 2005/0124831 A1    Jun. 9, 2005

(30) Foreign Application Priority Data

Mar. 8, 2002 (JP) ............................. 2002-064480

(51) Int. Cl.
*C07C 209/60* (2006.01)

(52) U.S. Cl. ...................................... 564/396; 564/471
(58) Field of Classification Search ................ None
See application file for complete search history.

(56) References Cited

U.S. PATENT DOCUMENTS 4,410,526 A    10/1983    Muchowski

OTHER PUBLICATIONS

Greenwood et al., Chemistry of the Elements, Pergamon Press Ltd., Oxford, 1985, p. 1337-1338.*
Wabnitz, T.C. et al., "Convenient synthesis of Cbz-protected β-amino ketones by a copper-catalyzed conjugate addition reaction", Tetrahedron Letters, vol. 43, No. 21 (2002), pp. 3891-3894.
Gaunt, M. J. et al., "Derailing the Wacker Oxidation: Development of a Palladium-Catalyzed Amidation Reaction", Organic Letters, vol. 3, No. 1 (2001), pp. 25-28.

* cited by examiner

*Primary Examiner*—Brian Davis
(74) *Attorney, Agent, or Firm*—Wenderoth, Lind & Ponack, L.L.P.

(57) ABSTRACT

A conjugate addition reaction between an α,β-unsaturated ketone compound and a carbamate compound is carried out to synthesize a β-aminoketone, a salt or a hydrate salt of a transition metal of Groups 7 to 11 of the Periodic Table of Elements being present in the reaction system as the catalyst. The novel method and the catalyst are capable of synthesizing the β-aminoketone by the Aza-Michael reaction with high yield and efficiency.

1 Claim, No Drawings

PROCESS FOR PRODUCING β-AMINOKETONE AND CATALYST THEREFOR

This application is a 371 of PCT/JP03/02715 filed Mar. 7, 2003.

TECHNICAL FIELD

The present invention relates to a method for producing a β-aminoketone and a catalyst therefor. The invention particularly relates to a novel method capable of highly efficiently synthesizing a β-aminoketone usable as a material or a synthetic intermediate for pharmaceuticals, perfumes, agricultural chemicals, polymers, etc. by an Aza-Michael reaction, and a novel Aza-Michael reaction catalyst useful in the method.

BACKGROUND ART

It has been known that structures having a nitrogen at the 1-position and an oxygen functional group at the 3-position are one of the most important units common in pharmaceuticals, etc. β-aminoketones are important intermediates for providing such important units.

Conjugate addition reactions of nitrogen nucleophiles with α,β-unsaturated compounds, called Aza-Michael reactions, are known as common methods for synthesizing the β-aminoketones to be used as the intermediates.

However, the conventional methods of synthesizing the β-aminoketones by the Aza-Michael reactions are disadvantageous in that these are inefficient reaction processes, selectivity and yield not always being satisfactory. Under such circumstances, Spencer, et al. have recently reported a method of using a carbamate as a nitrogen nucleophile in the presence of a $PdCl_2(CH_3CN)_2$ complex catalyst (*Org. Lett.*, 2001, 3, 25).

However, also in the method using the $PdCl_2(CH_3CN)_2$ complex catalyst, there are restrictions in the types of the (α,β-unsaturated ketones and the carbamates and the reaction conditions, and yield and efficiency of the reaction are insufficient for practical use.

Accordingly, an object of the invention is to overcome the conventional problems, thereby providing a novel technology for synthesizing various β-aminoketones by an Aza-Michael reaction with high yield and efficiency.

DISCLOSURE OF THE INVENTION

To solve the above problems, according to a first aspect of the present invention, there is provided a method for producing a β-aminoketone, characterized in that a conjugate addition reaction between an α,β-unsaturated ketone compound and a carbamate compound is carried out to synthesize the β-aminoketone, a salt or a hydrate salt of a transition metal of Groups 7 to 11 of the Periodic Table of Elements being present in the reaction system as a catalyst.

According to a second aspect of the invention, there is provided the method for producing a β-aminoketone characterized in that the salt or the hydrate salt of the transition metal is a halide, a perhalogenate, or a hydrate thereof. According to a third aspect, there is provided the method for producing a β-aminoketone characterized in that the transition metal is at least one of the group consisting of Fe, Ru, Rh, Re, Os, Ir, Pt, and Au.

Further, according to a fourth aspect of the invention, there is provided a catalyst for a conjugate addition reaction of a nitrogen nucleophile to an α,β-unsaturated compound, characterized in that the catalyst is a salt or a hydrate salt of a transition metal of Groups 7 to 11 of the Periodic Table of Elements. According to a fifth aspect, there is provided the catalyst characterized in that the salt or the hydrate salt of the transition metal is a halide, a perhalogenate, or a hydrate thereof. According to a sixth aspect, there is provided the catalyst characterized in that the transition metal is at least one of the group consisting of Fe, Ru, Rh, Re, Os, Ir, Pt, and Au. According to a seventh aspect, there is provided the catalyst characterized in that the catalyst is for a conjugate addition reaction of a carbamate compound to an α,β-unsaturated ketone compound.

BEST MODE FOR CARRYING OUT THE INVENTION

The present invention is characterized by the above aspects. An embodiment of the invention is described below.

In the invention, a β-aminoketone is synthesized from an (α,β-unsaturated ketone compound and a carbamate compound by an Aza-Michael reaction. For example, the α,β-unsaturated ketone compound may be represented by the following formula:

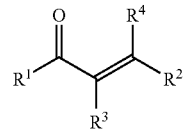

wherein $R^1$ and $R^2$ represent the same or different hydrocarbon groups that may have a substituent, $R^2$ and $R^3$ each represent a hydrogen atom or hydrocarbon group that may have a substituent where $R^2$ and $R^3$ may be the same or different, and $R^1$, $R^2$, $R^3$ or $R^4$ may be bonded to form a ring as a carbon chain. The carbamate compound may be represented by the following formula:

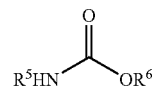

wherein $R^5$ represents a hydrogen atom or a hydrocarbon group that may have a substituent, $R^6$ represents a hydrocarbon group that may have a substituent, and $R^5$ and $R^6$ may be bonded to form a ring as a carbon chain.

The above hydrocarbon groups may be selected from aliphatic or alicyclic, saturated or unsaturated hydrocarbon groups, aromatic groups, and heterocyclic groups, and, similar to the case of the heterocyclic group, may have a substituent such as a hydrocarbon group and an alkoxy group, as long as the substituent do not inhibit the reaction.

For example, the Aza-Michael reaction can produce a β-aminoketone represented by the following formula.

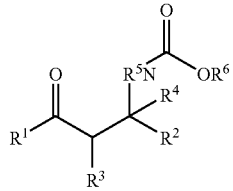

In this invention, a salt or a hydrate salt of a transition metal of Groups 7 to 11 of the Periodic Table of Elements is used as a reaction catalyst in the synthesis of the β-aminoketone by the Aza-Michael reaction. The hydrate salt means a hydrate of a transition metal salt.

The transition metals of Groups 7 to 11 include Fe, Co, Ni, Mn, Cu, Ru, Rh, Pd, Ag, Re, Os, Ir, Pt, Au, etc. In the invention, more preferred transition metals are Fe, Ru, Rh, Re, Os, Ir, Pt, and Au.

An inorganic acid salt of the transition metal, a hydrate thereof, or an organic acid salt is used in the invention. The catalyst is more preferably a halide or perhalogenate of the transition metal, or a hydrate thereof. Specifically, examples of the preferred catalysts include $ReCl_5$, $Fe(ClO_4)_3 \cdot 9H_2O$, $RuCl_3 \cdot nH_2O$, $OsCl_3 \cdot 3H_2O$, $RhCl_3 \cdot 3H_2O$, $IrCl_4 \cdot nH_2O$, $PtCl_4 \cdot 5H_2O$, AuCl, and $AuCl_3 \cdot 2H_2O$.

In the reaction, the mole ratio of the α,β-unsaturated ketone compound to the carbamate compound may be roughly within the range of 1/10 to 10/1 in general. Further, the amount of the catalyst may be approximately 0.01 to 0.5 mol per 1 mol of the α,β-unsaturated ketone compound.

A solvent may be used in the reaction, and examples of the preferred solvents include halogenated hydrocarbon solvents such as dichloromethane, and aromatic hydrocarbons such as toluene.

In general, the reaction may be carried out at approximately −10 to 50° C., for instance at 18 to 25° C., in the air or an inert atmosphere. The reaction may be carried out appropriately under an atmospheric pressure, an increased pressure, or a reduced pressure.

The transition metal salt catalyst can be effectively used in the reaction for synthesizing the β-aminoketone, and further the use of the catalyst is not limited thereto, the catalyst being effective for conjugate addition reactions of nitrogen nucleophiles with α,β-unsaturated compounds.

Also in the case of an α,β-unsaturated enone compound having a substituent at the α-position, etc., the catalyst effectively accelerates the above conjugate addition.

The invention will be explained in more detail referring to Examples below without intention of restricting the invention.

EXAMPLES

Example 1

An (α,β-unsaturated ketone compound (enone) (1a) (0.250 mmol, 1 equivalent) and a carbamate compound (2a) (0.375 mmol, 1.5 equivalents) were added to 1 ml of a dichloromethane solution of $PtCl_4 \cdot 5H_2O$ (0.025 mmol, 0.1 equivalents), and stirred at room temperature (about 20° C.) for 2 hours, in accordance with the following reaction formula.

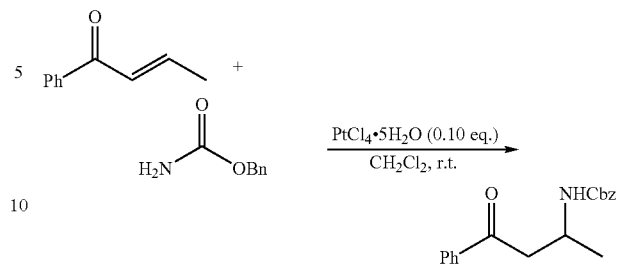

Then, to the reaction mixture was added sat. $NaHCO_3$, and the aqueous phase was subjected to extraction with dichloromethane. The entire organic phase was dried over $Na_2SO_4$, filtered, and evaporated.

Thus obtained crude product was purified by a thin layer TLC to obtain the desired β-aminoketone (3a), and the yield was 82%.

Example 2

The reaction of synthesizing the β-aminoketone (3a) of Example 1 was carried out using various metal salts instead of the platinum halide hydrate.

The results are shown in the following table.

TABLE 1

| Metal salt | Reaction time (h) | Yield (%) |
|---|---|---|
| $BF_3 \cdot OEt_2$ | 2 | 20 |
| $AlCl_3$ | 6 | trace |
| $TiCl_4$ | 2 | 6 |
| $Sc(oTf)_3$ | 6 | 5 |
| $Cr(ClO_4)_3 \cdot 6H_2O$ | 6 | 31 |
| $YCl_3 \cdot 6H_2O$ | 2 | 15 |
| $ReCl_5$ | 6 | 96 |
| $Fe(ClO_4)_3 \cdot 9H_2O$ | 6 | 86 |
| $RuCl_3 \cdot nH_2O$ | 6 | 78 |
| $OsCl_3 \cdot 3H_2O$ | 6 | 96 |
| $RhCl_3 \cdot 3H_2O$ | 6 | 94 |
| $IrCl_4 \cdot nH_2O$ | 2 | quant. |
| $PtCl_4 \cdot 5H_2O$ | 2 | 82 |
| AuCl | 6 | quant. |
| $AuCl_3 \cdot 2H_2O$ | 2 | 91 |

As shown in Table 1, although the conventionally well-known Lewis acids of $BF_3 \cdot OEt_2$, $AlCl_3$, and $TiCl_4$ hardly showed any activity in the reaction, the catalysts of the invention, the halides and the perchlorates of the transition metals of Groups 7 to 11 and the hydrates thereof, showed remarkable activity. The catalysts of the invention enabled the β-aminoketone (3a) to be synthesized with high reaction yield.

Example 3

Various α,β-unsaturated ketone compounds (enones) and carbamate compounds were reacted with each other in the same manner as Example 1 using various salts or hydrates of the transition metals of the invention as the catalysts.

For comparison, a known $PdCl_2(CH_3CN)_2$ complex was also used. The results are shown in Table 2. The superscript[b] in Table 2 means that the ratio of the enone to the carbamate compound was 2/1.

TABLE 2

| enones | nucleophiles | adducts | catalysts | time/h | yield/% |
|---|---|---|---|---|---|
| 1a (Ph-CH=CH-C(O)-... chalcone-type) | 2a (H$_2$N-C(O)-OBn) | 3a (Ph-C(O)-CH$_2$-CH(NHCbz)-CH$_3$) | Fe(ClO$_4$)$_3$·9H$_2$O | 6 | 88 |
| | | | RhCl$_3$·3H$_2$O | 6 | 94 |
| | | | IrCl$_4$·nH$_2$O | 2 | quant. |
| | | | PtCl$_4$·5H$_2$O | 2 | 82 |
| | | | AuCl$_3$·2H$_2$O | 2 | quant. |
| | | | AuCl | 6 | 91 |
| | | | ReCl$_5$ | 6 | 96 |
| 1a | MeHN-C(O)-OBn | Ph-C(O)-CH$_2$-CH(NMeCbz)-CH$_3$ | PtCl$_4$·5H$_2$O | 24 | quant. |
| 1a | oxazolidinone (HN-CH$_2$-CH$_2$-O-C(O)) | N-substituted oxazolidinone adduct | IrCl$_4$·nH$_2$O | 48 | 50 |
| | | | PtCl$_4$·5H$_2$O | 48 | 96 |
| | | | AuCl | 48 | 54 |
| | | | ReCl$_5$ | 48 | 82 |
| (CH$_3$)$_2$C=CH-C(O)-CH$_3$ | 2a | (CH$_3$)$_2$C(NHCbz)-CH$_2$-C(O)-CH$_3$ | PtCl$_4$·5H$_2$O | 24 | 59 |
| | | | PtCl$_4$·5H$_2$O | 20 | 80[b] |
| | | | AuCl$_3$·2H$_2$O | 20 | 51 |
| | | | AuCl | 20 | 65 |
| CH$_3$-CH=C(CH$_3$)-C(O)-CH$_3$ | 2a | CH$_3$-CH(NHCbz)-CH(CH$_3$)-C(O)-CH$_3$ (methylated adduct) | PtCl$_4$·5H$_2$O | 24 | 66 |
| | | | PtCl$_4$·5H$_2$O | 20 | 75[b] |
| | | | AuCl$_3$·2H$_2$O | 20 | 78 |
| | | | AuCl | 20 | 57 |
| Ph-C(O)-C(CH$_3$)=CH-CH$_3$ | 2a | Ph-C(O)-CH(CH$_3$)-CH(NHCbz)-CH$_3$ | PtCl$_4$·5H$_2$O | 20 | 65 |
| | | | PtCl$_4$·5H$_2$O | 20 | 83[b] |
| | | | PdCl$_2$(CH$_3$CN)$_2$ | 20 | 11 |
| Ph-C(O)-C(CH$_3$)=CH$_2$ | 2a | Ph-C(O)-CH(CH$_3$)-CH$_2$-NHCbz | PtCl$_4$·5H$_2$O | 20 | 69 |
| | | | PdCl$_2$(CH$_3$CN)$_2$ | 20 | 9 |
| Ph-C(O)-C(Et)=CH$_2$ | 2a | Ph-C(O)-CH(Et)-CH$_2$-NHCbz | PtCl$_4$·5H$_2$O | 20 | 52 |
| | | | PtCl$_4$·5H$_2$O | 20 | 68[b] |
| | | | PdCl$_2$(CH$_3$CN)$_2$ | 20 | 3 |
| cyclohex-2-enone | 2a | 3-(NHCbz)-cyclohexanone | PtCl$_4$·5H$_2$O | 24 | 42 |
| | | | PtCl$_4$·5H$_2$O | 20 | 65[b] |

It was confirmed also from Table 2 that the method of the invention enabled the β-aminoketones having various structures to be synthesized with high reaction yield.

INDUSTRIAL APPLICABILITY

As described in detail above, according to the present invention, there are provided the novel method and the novel catalyst capable of synthesizing a β-aminoketone by an Aza-Michael reaction with high yield and efficiency.

The invention claimed is:

1. A method for producing a β-aminoketone, wherein a conjugate addition reaction between an α,β-unsaturated ketone compound and a carbamate compound is carried out to synthesize the β-aminoketone, and a salt or a hydrate salt of a transition metal of Groups 7 to 11 of the Periodic Table of Elements is present in the reaction system as a catalyst, and the salt or hydrate salt of the transition metal is at least one member selected from the group consisting of ReCl$_5$, Fe(ClO$_4$)$_3$·9H$_2$O, RuCl$_3$·nH$_2$O, OsCl$_3$·3H$_2$O, RhCl$_3$·3H$_2$O, IrCl$_4$·nH$_2$O, PtCl$_4$·5H$_2$O, AuCl, and AuCl$_3$·2H$_2$O.

* * * * *